United States Patent
Park et al.

(10) Patent No.: US 12,156,892 B2
(45) Date of Patent: Dec. 3, 2024

(54) STRAIN HAVING ACTIVITY OF REDUCING ADVANCED GLYCATION END PRODUCTS AND USE THEREOF

(71) Applicant: Korea Food Research Institute, Jeollabuk-do (KR)

(72) Inventors: Ho Young Park, Gyeonggi-do (KR); Yoon Sook Kim, Seoul (KR); Sang Hoon Lee, Gyeonggi-do (KR); Sang Keun Ha, Gyeonggi-do (KR); So Young Lee, Gyeonggi-do (KR); Mi Jin Oh, Jeollabuk-do (KR)

(73) Assignee: Korea Food Research Institute, Jeollabuk-do (KR)

( * ) Notice: Subject to any disclaimer, the term of this patent is extended or adjusted under 35 U.S.C. 154(b) by 0 days.

(21) Appl. No.: 16/500,913

(22) PCT Filed: Apr. 6, 2018

(86) PCT No.: PCT/KR2018/004076
§ 371 (c)(1),
(2) Date: Oct. 4, 2019

(87) PCT Pub. No.: WO2018/186710
PCT Pub. Date: Oct. 11, 2018

(65) Prior Publication Data
US 2020/0270709 A1 Aug. 27, 2020

(30) Foreign Application Priority Data

Apr. 6, 2017 (KR) .................. 10-2017-0044938
Apr. 6, 2017 (KR) .................. 10-2017-0044949
Jun. 23, 2017 (KR) .................. 10-2017-0079726
Jun. 23, 2017 (KR) .................. 10-2017-0079735

(51) Int. Cl.

| | |
|---|---|
| *A61K 35/744* | (2015.01) |
| *A23K 10/18* | (2016.01) |
| *A23L 33/135* | (2016.01) |
| *A61K 35/742* | (2015.01) |
| *A61K 35/747* | (2015.01) |
| *C12N 1/20* | (2006.01) |
| *C12R 1/125* | (2006.01) |
| *C12R 1/225* | (2006.01) |

(52) U.S. Cl.
CPC .......... *A61K 35/744* (2013.01); *A23K 10/18* (2016.05); *A23L 33/135* (2016.08); *A61K 35/742* (2013.01); *A61K 35/747* (2013.01); *C12N 1/20* (2013.01); *C12N 1/205* (2021.05); *A23V 2002/00* (2013.01); *A23V 2400/165* (2023.08); *A23V 2400/167* (2023.08); *A23V 2400/231* (2023.08); *C12R 2001/125* (2021.05); *C12R 2001/225* (2021.05)

(58) Field of Classification Search
CPC ............ A23V 2002/00; A23Y 2220/63; A23Y 2220/65; A23Y 2240/41; A23K 10/16; A23K 10/18; A23L 33/135; A23L 5/20; A61K 2035/115; A61K 35/742; A61K 35/747; A61K 35/744; C12N 1/20; C12N 1/205; C12R 1/125; C12R 1/225; C12R 2001/125; C12R 2001/225
See application file for complete search history.

(56) References Cited

U.S. PATENT DOCUMENTS

| | | | |
|---|---|---|---|
| 9,381,223 B2 | 7/2016 | Shimoda et al. | |
| 2011/0038891 A1* | 2/2011 | Hara | A61P 37/08 424/234.1 |
| 2011/0268702 A1* | 11/2011 | Fukushima | A61K 31/733 424/93.3 |

(Continued)

FOREIGN PATENT DOCUMENTS

| | | |
|---|---|---|
| JP | 2006256993 A | 9/2006 |
| JP | 2014108932 A | 6/2014 |

(Continued)

OTHER PUBLICATIONS

Fu, M et al. The advanced glycation end product, Ne-(carboxymethyl)lysine, is a product of both lipid peroxidation and glycoxidation reactions. The Journal of Biological Chemistry. 1996. 271(17): 9982-9986. (Year: 1996).*

(Continued)

*Primary Examiner* — David W Berke-Schlessel
*Assistant Examiner* — Susan E. Fernandez
(74) *Attorney, Agent, or Firm* — Servilla Whitney LLC

(57) ABSTRACT

The present invention relates to a novel strain having the activity of reducing advanced glycation end products and a use thereof and, more particularly, to a food composition having the activity of reducing advanced glycation end products and a pharmaceutical composition for preventing or treating a disease caused by advanced glycation end products each of which comprises a *Lactococcus lactis* KF140 (accession number KCCM11673P) strain, a *Bacillus subtilis* KF11 (accession number KCCM11981P) strain, a *Lactobacillus pentosus* KF8 (accession number KCCM11997P) strain, or a *Lactobacillus paracasei* KF00816 (accession number KCCM11998P) strain, which are all novel strains; a lysate thereof; or a culture thereof as an active ingredient. In addition, the present invention relates to a composition for intestinal regulation, a probiotic composition, a feed composition, and a fermented product, each of which comprises the novel strain of the present invention, a lysate thereof, or a culture thereof as an active ingredient.

8 Claims, 8 Drawing Sheets
Specification includes a Sequence Listing.

(56) References Cited

U.S. PATENT DOCUMENTS

| | | | |
|---|---|---|---|
| 2014/0079676 | A1 | 3/2014 | Olmstead |
| 2014/0335262 | A1* | 11/2014 | Okuhata .............. A23L 11/50 435/252.5 |

FOREIGN PATENT DOCUMENTS

| | | | | | |
|---|---|---|---|---|---|
| JP | 2015182954 | A | | 10/2015 | |
| JP | 5935155 | B2 | * | 6/2016 | |
| JP | 5940872 | B2 | | 6/2016 | |
| KR | 20050027338 | A | | 3/2005 | |
| KR | 20080107193 | A | | 12/2008 | |
| KR | 20120089970 | A | | 8/2012 | |
| KR | 20140050415 | A | * | 4/2014 | |
| KR | 20150045420 | A | | 4/2015 | |
| KR | 20160029019 | A | | 3/2016 | |
| KR | 20160100658 | A | | 8/2016 | |
| KR | 20160126605 | A | | 11/2016 | |
| KR | 20160132050 | A | | 11/2016 | |
| KR | 20170020679 | A | * | 2/2017 | ........... A23L 33/135 |
| WO | WO-2007119693 | A1 | * | 10/2007 | ........... A61K 35/747 |

OTHER PUBLICATIONS

Jung, JY et al. Kimchi microflora: history, current status, and perspectives for industrial kimchi production. Appl. Microbiol. Biotechnol. 2014. 98: 2385-2393. (Year: 2014).*

Nonaka, Y et al. Antiallergic effects of Lactobacillus pentosus strain S-PT84 mediated by modulation of Th1/Th2 immunobalance and induction of IL-10 production. Int. Arch. Allergy Immunol. 2008. 145: 249-257. (Year: 2008).*

Luh, BS. Industrial production of soy sauce. Journal of Industrial Microbiology. 1995. 14: 467-471. (Year: 1995).*

Shin, H et al. Preventive effects of a probiotic mixture in a ovalbumin-induced food allergy model. J. Microbiol. Biotechnol. 2018. 28(1): 65-76. First published online on Nov. 9, 17. (Year: 2017).*

OM nucleic search of SEQ ID No. 2 of Published Applications. Performed on Apr. 30, 2021. (Year: 2021).*

OM nucleic search of SEQ ID No. 3 of Published Applications. Performed on Apr. 30, 2021. (Year: 2021).*

BLAST alignment of H-61 strain of JP 5935155 with SEQ ID No. 1. [online]. [retrieved on Aug. 4, 2022]. Retrieved from the Internet: <https://blast.ncbi.nlm.nih.gov/Blast.cgi>. (Year: 2022).*

BLAST alignment of ATCC 8041 strain of Ugajin with SEQ ID No. 4. [online]. [retrieved on Aug. 4, 2022]. Retrieved from the Internet: <https://blast.ncbi.nlm.nih.gov/Blast.cgi>. (Year: 2022).*

BLAST alignment of ST11 strain of Fukushima with SEQ ID No. 3. [online]. [retrieved on Aug. 4, 2022]. Retrieved from the Internet: <https://blast.ncbi.nlm.nih.gov/Blast.cgi>. (Year: 2022).*

Toda, M et al. The Maillard reaction and food allergies: is there a link? Clin. Chem. Lab. Med. 2014. 52(1): 61-67 (Year: 2014).*

Khangholi, S et al. The mechanisms of inhibition of advanced glycation end products formation through polyphenols in hyperglycemic condition. Planta Med. 2016. 82: 32-45. Published online Nov. 9, 2015. (Year: 2015).*

Pereira, Thiago Melo Costa, et al., "Coadjuvants in the Diabetic Complications: Nutraceuticals and Drugs with Pleiotropic Effects", International Journal of Molecular Sciences 2016, 17, 1273, Aug. 5, 2016, 1-24.

Yadav, Hariom, et al., "Effect of Dahi Containing Lactococcus lactis on the Progression of Diabetes Induced by a High-Fructose Diet in Rats", Bioscience, Biotechnology, and Biochemistry, 70 (5), 2006, May 22, 2014, 1255-1258.

* cited by examiner

Fig.1

| Sample | DR. PROBA BABY (commercial product-01) | LACPIDO PREMIUM (commercial product-02) | LACTO-FIT alive lactic acid bacteria GOLD (commercial product-03) | Proslab Family (commercial product-04) |
|---|---|---|---|---|
| Manufacturer | CTC BIO | Food & Drugs networks | Chong Kun Dang | ProsLab |
| Lactic acid bacteria | Lactobacillus reuteri<br>Lactobacillus rhamnosus<br>Lactobacillus casei<br>Lactobacillus plantarum<br>Enterococcus faecium<br>Bifidobacterium infantis<br>Bifidobacterium bifidum<br>Bifidobacterium animalis ssp. Lactis | Lactobacillus acidophillus<br>Lactobacillus fermentum<br>Lactobacillus casei<br>Lactobacillus faecium<br>Bifidobacterium bifidum<br>Bifidobacterium longum | Lactobacillus acidophillus<br>Lactobacillus fermentum<br>Lactobacillus bifidum<br>Bifidobacterium animalis ssp. Lactis<br>Streptococcus thermophilus<br>Enterococcus faecium | Lactobacillus plantarum<br>Lactobacillus casei<br>Lactobacillus acidophillus<br>Lactobacillus rhamnosus<br>Enterococcus faecium<br>Bifidobacterium animalis ssp. Lactis<br>Bifidobacterium bifidum<br>Bifidobacterium breve<br>Bifidobacterium longum<br>Bacillus coagulans |

| Sample | STRONG BIOTICS (commercial product-05) | Superbiotics (commercial product-06) | PROBIOTICS lactic acid bacteria VSL#3 (commercial product-07) |
|---|---|---|---|
| Manufacturer | Christian Hansen | CENOVIS | VSL |
| Lactic acid bacteria | Bifidobacterium animalis ssp<br>Lactobacillus acidophillus<br>Lactobacillus delbrueckii subsp. Bulgaricus<br>Streptococcus thermophilu | Lactobacillus plantarum | Lactobacillus acidophillus<br>Lactobacillus fermentum<br>Lactobacillus casei<br>Lactobacillus faecium<br>Bifidobacterium bifidum<br>Bifidobacterium longum |

STRAIN HAVING ACTIVITY OF REDUCING ADVANCED GLYCATION END PRODUCTS AND USE THEREOF

CROSS-REFERENCE TO RELATED APPLICATIONS

This application is the National Stage entry of PCT/KR2018/004076, filed on Apr. 6, 2018, which claims priority to Korean Application Numbers 10-2017-0044938, filed on Apr. 6, 2017, 10-2017-0044949 filed on Apr. 6, 2017, 10-2017-0079726 filed on Jun. 23, 2017 and 10-2017-0079735 filed Jun. 23, 2017, which are incorporated herein by reference in their entireties.

TECHNICAL FIELD

The present invention relates to a novel strain having the activity of reducing advanced glycation end products and a use thereof.

CROSS-REFERENCE TO SEQUENCE LISTING

The Sequence Listing identified as "CNP0009-00US_SeqList_ST25.txt" (8,473 bytes), created Mar. 6, 2020, is hereby incorporated by reference.

BACKGROUND ART

Nonenzymatic glycation reaction of proteins refers to Maillard reaction occurring between an amino acid group of a protein, such as lysine residue, and a reducing sugar without enzymatic action, which leads to the formation of advanced glycation end products (AGEs). Nonenzymatic glycation reaction of proteins is a reaction in which a free amino group of a protein, such as lysine or arginine, reacts with a carbonyl group of a reducing sugar to form an initial glycation reaction product, Schiff base, and the compounds formed therefrom continually produce a brown compound (melanoidine) through a series of complex reactions, such as condensation, rearrangement, oxidation, cleavage, cyclization, which leads to the formation of irreversible advanced glycation end products in general concept.

The advanced glycation end product is an irreversible reaction product. Therefore, even if blood glucose level is recovered normally, the product formed once is not decomposed and accumulates in the tissues during the life of the protein, resulting in an abnormal change of the structure and function of the tissues. Glycation reaction easily occurs in a collagen with a relatively long half-life, and the advanced glycation end products formed once form a cross-linkage with a collagen to result in an abnormal physicochemical change of the structure in the body, other proteins of connective tissue, and the like. In addition, it is recognized by a specific receptor for various types of cells, which leads to the cause of diseases, such as diabetes, diabetes complications, such as diabetic retinopathy, diabetic neuropathy, diabetic cataract, diabetic nephropathy, chronic kidney disease, heart disease, vascular disease, and aging.

Therefore, studies have been in progress to inhibit the production of such advanced glycation end products. One of the representative synthetic pharmaceutical products is aminoguanidine, a nucleophilic hydrazine, which is bound with a product of condensation reaction to inhibit the production of advanced glycation end products, resulting in the prevention of the development of complications. In addition, aminoguanidine is the most promising pharmaceutical product for the prevention and treatment of diabetes complications, and thus, it has been studied in a phase 3 clinical trial. However, it was found that there was a problem of toxicity induced by prolonged administration of aminoguanidine, which calls a need for the development of safer pharmaceutical products.

Thus, there is a need for the development of a new ingredient which can inhibit and reduce advanced glycation end products and which secures no side effects for human body and stability.

In this aspect, the present invention has been completed by isolating and identifying the novel strains which can remarkably reduce the advanced glycation end products, and identifying the activity of the novel strains.

DETAILED DESCRIPTION OF THE INVENTION

Technical Problem

It is therefore an object of the present invention to provide a novel strain having the activity of reducing advanced glycation end products (AGEs), characterized in that it is selected from the group consisting of a *Lactococcus lactis* KF140 (accession number KCCM11673P) strain, a *Bacillus subtilis* KF11 (accession number KCCM11981P) strain, a *Lactobacillus pentosus* KF8 (accession number KCCM11997P) strain, and a *Lactobacillus paracasei* KF00816 (accession number KCCM11998P) strain.

It is another object of the present invention to provide a food composition having the activity of reducing advanced glycation end products, comprising the novel strain of the present invention, a lysate thereof, or a culture thereof as an active ingredient.

It is another object of the present invention to provide a pharmaceutical composition for preventing or treating a disease related to advanced glycation end products, comprising the novel strain of the present invention, a lysate thereof, or a culture thereof as an active ingredient.

It is another object of the present invention to provide a composition for intestinal regulation, comprising the novel strain of the present invention, a lysate thereof, or a culture thereof as an active ingredient.

It is another object of the present invention to provide a probiotic composition comprising the novel strain of the present invention, a lysate thereof, or a culture thereof as an active ingredient.

It is another object of the present invention to provide a feed composition comprising the novel strain of the present invention, a lysate thereof, or a culture thereof as an active ingredient.

It is another object of the present invention to provide a fermented product comprising the novel strain of the present invention, a lysate thereof, or a culture thereof as an active ingredient.

Further, it is another object of the present invention to provide a method for inhibiting advanced glycation end products, by using the novel strain of the present invention, a lysate thereof, or a culture thereof.

Solution to Problem

The present invention provides a novel strain having the activity of reducing advanced glycation end products (AGEs), characterized in that it is selected from the group consisting of a *Lactococcus lactis* KF140 (accession number KCCM11673P) strain, a *Bacillus subtilis* KF11 (accession number KCCM11981P) strain, a *Lactobacillus pentosus* KF8 (accession number KCCM11997P) strain, and a *Lactobacillus paracasei* KF00816 (accession number KCCM11998P) strain.

In one embodiment of the present invention, the advanced glycation end products (AGEs) as described above may be nonfluorescent advanced glycation end products.

In addition, the present invention provides a food composition having the activity of reducing advanced glycation end products, comprising the novel strain of the present invention, a lysate thereof, or a culture thereof as an active ingredient.

In one embodiment of the present invention, the above composition may prevent or improve diabetes, chronic kidney disease, heart disease, vascular disease, diabetic retinopathy, diabetic neuropathy, diabetic cataract, or diabetic nephropathy, which may be caused by advanced glycation end products.

In addition, the present invention provides a pharmaceutical composition for preventing or treating a disease related to advanced glycation end products, comprising the novel strain of the present invention, a lysate thereof, or a culture thereof as an active ingredient.

In one embodiment of the present invention, the above disease may be selected from the group consisting of diabetes, chronic kidney disease, heart disease, vascular disease, diabetic retinopathy, diabetic neuropathy, diabetic cataract, and diabetic nephropathy.

In addition, the present invention provides a composition for intestinal regulation, comprising the novel strain of the present invention, a lysate thereof, or a culture thereof as an active ingredient.

In addition, the present invention provides a probiotic composition comprising the novel strain of the present invention, a lysate thereof, or a culture thereof as an active ingredient.

In addition, the present invention provides a feed composition comprising the novel strain of the present invention, a lysate thereof, or a culture thereof as an active ingredient.

In addition, the present invention provides a fermented product comprising the novel strain of the present invention, a lysate thereof, or a culture thereof as an active ingredient.

Further, the present invention provides a method for inhibiting advanced glycation end products, by using the novel strain of the present invention, a lysate thereof, or a culture thereof.

Effect of Invention

The present invention has isolated and identified a *Lactococcus lactis* KF140 (accession number KCCM11673P) strain, a *Bacillus subtilis* KF11 (accession number KCCM11981P) strain, a *Lactobacillus pentosus* KF8 (accession number KCCM11997P) strain, and a *Lactobacillus paracasei* KF00816 (accession number KCCM11998P) strain, which are all novel, and the present invention has investigated a novel use of these strains. The above strain isolated and identified in the present invention, a lysate thereof, or a culture thereof has the activity of effectively reducing advanced glycation end products. Therefore, there is an effect that it may be used in the preparation of a functional food and a pharmaceutical product for preventing or treating a disease caused by advanced glycation end products, and further, it may be used in the preparation of a composition for intestinal regulation, a probiotic composition, a feed composition, and a fermented product.

BRIEF DESCRIPTION OF DRAWINGS

FIG. 1 shows the commercially available probiotic products used as a control group in one example of the present invention.

BEST EMBODIMENT FOR WORKING THE INVENTION

Figure 2:
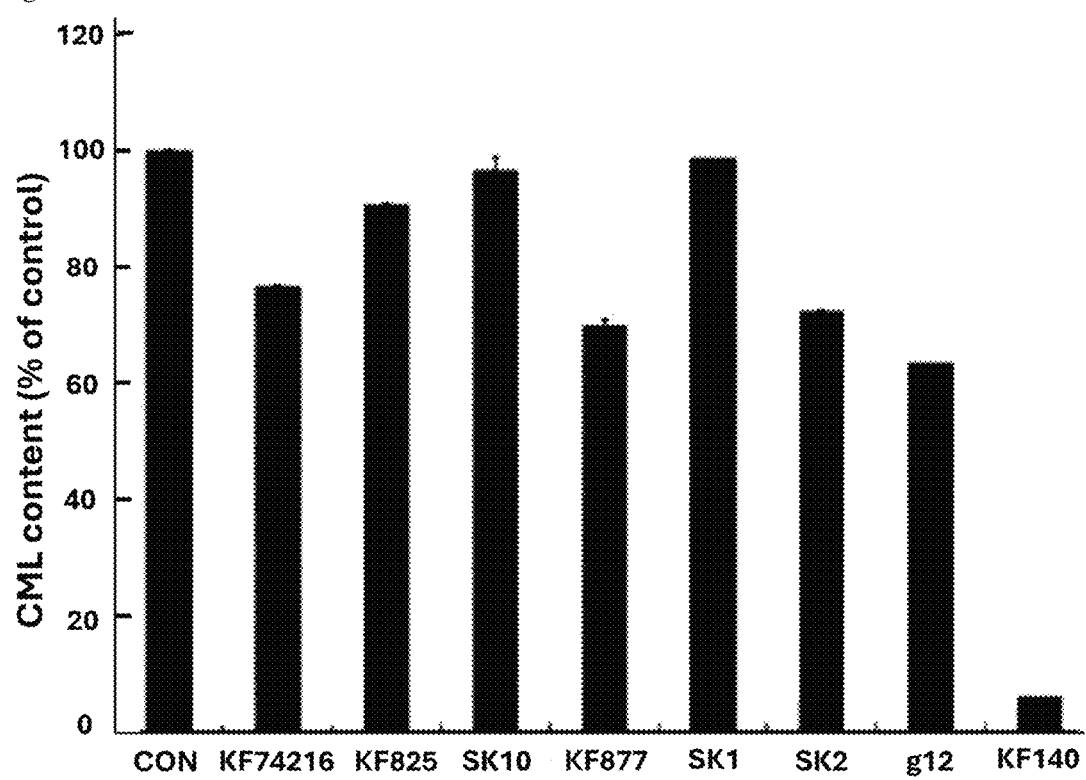
FIG. 2 shows the result of comparative analysis of the activity of reducing CML, wherein a *Lactococcus lactis* KF140 strain of the present invention and other lactic acid bacteria are used as a subject.
Figure 3:
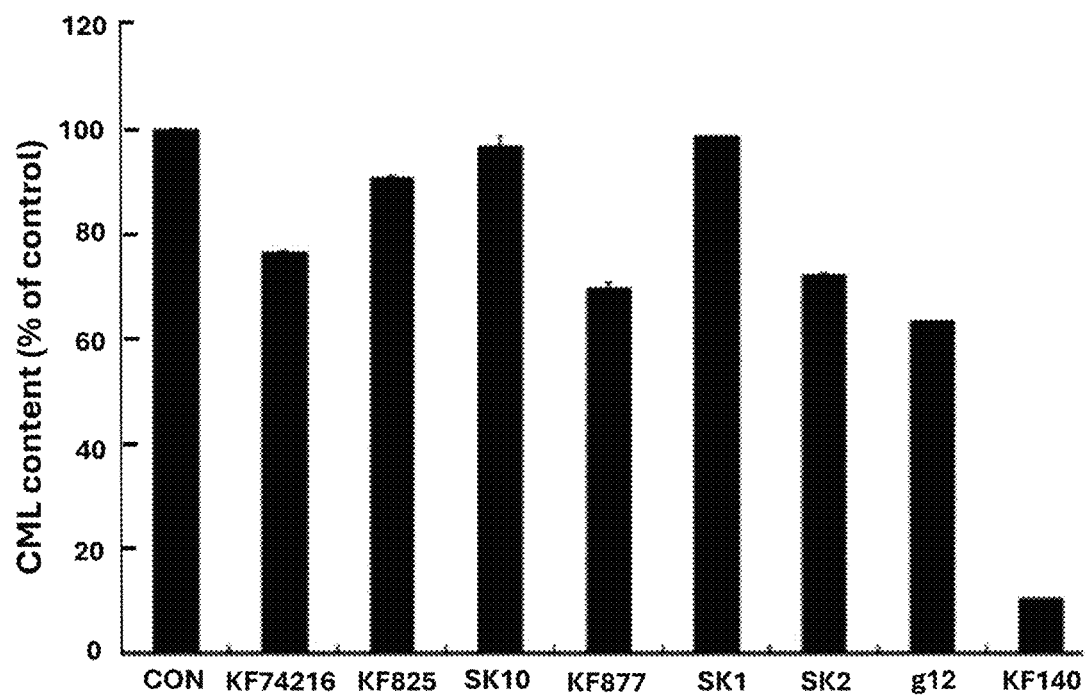
FIG. 3 shows the result of comparative analysis of the activity of reducing CML, wherein a *Bacillus subtilis* KF11 strain of the present invention and other lactic acid bacteria are used as a subject.
Figure 4:
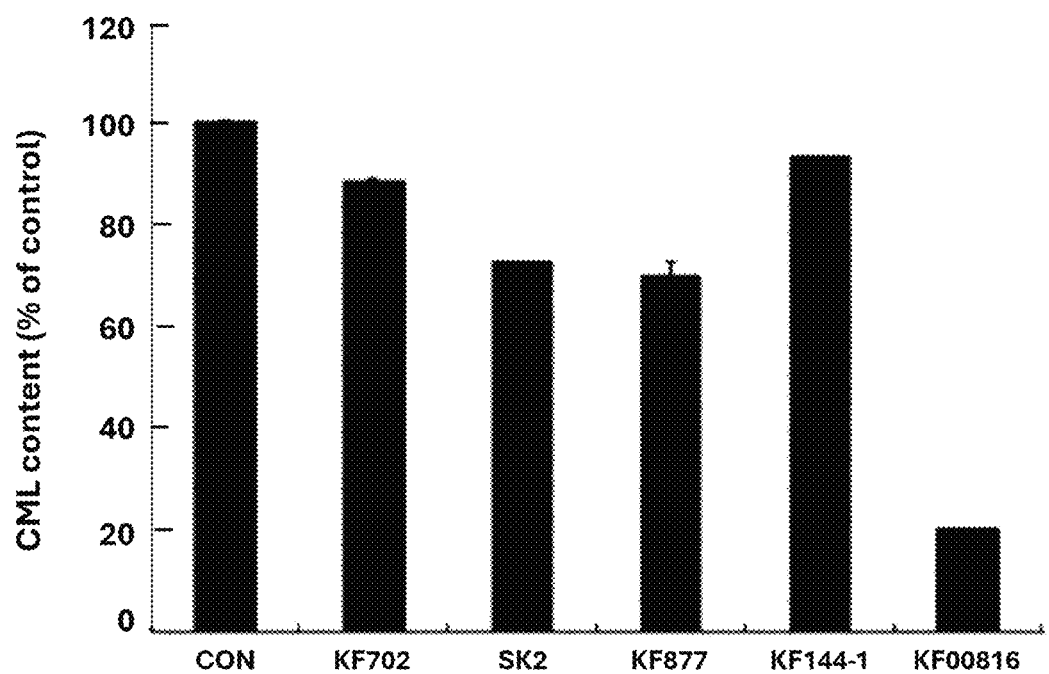
FIG. 4 shows the result of comparative analysis of the activity of reducing CML, wherein a *Lactobacillus paracasei* KF00816 strain of the present invention and other lactic acid bacteria are used as a subject.
Figure 5:
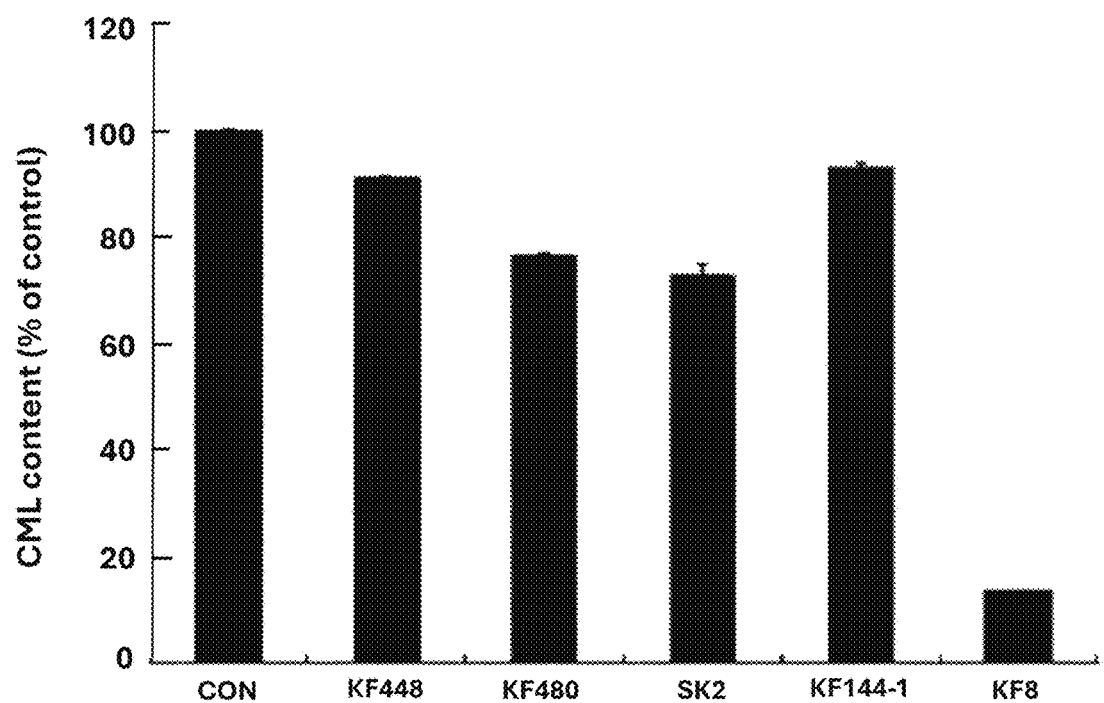
FIG. 5 shows the result of comparative analysis of the activity of reducing CML, wherein a *Lactobacillus pentosus* KF8 strain of the present invention and other lactic acid bacteria are used as a subject.
Figure 6:
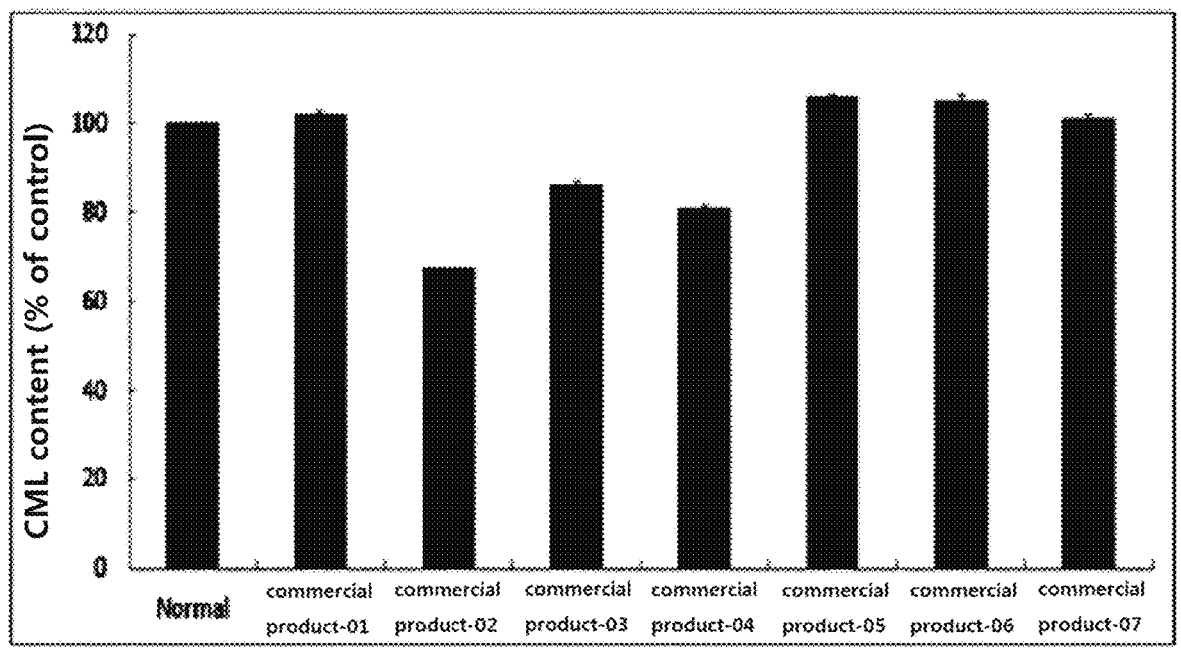
FIG. 6 shows the result of analysis of the activity of reducing CML of the commercially available probiotic products.

The present invention is characterized in that it isolated and identified a *Lactococcus lactis* KF140 (accession number KCCM11673P) strain, a *Bacillus subtilis* KF11 (accession number KCCM11981P) strain, a *Lactobacillus pentosus* KF8 (accession number KCCM11997P) strain, and a *Lactobacillus paracasei* KF00816 (accession number KCCM11998P) strain, which are all novel, and the present invention first investigated their activity of inhibiting the production of advanced glycation end products.

The advanced glycation end product is an irreversible reaction product. Therefore, even if blood glucose level is recovered normally, the product formed once is not decomposed and accumulates in the tissues during the life of the protein to result in an abnormal change of the structure and function of the tissues, which leads to the cause of various diseases, such as diabetes, diabetes complications, chronic kidney disease, heart disease, vascular disease, or aging. Therefore, various diseases derived from advanced glycation end products may be prevented, improved, or treated by inhibiting or reducing the production of advanced glycation end products.

Meanwhile, a kind of advanced glycation end products includes fluorescent substances, such as pentosidine or argpyrimidine, and nonfluorescent substances, such as N-carboxymethyl lysine (CML), N-carboxyethyl lysine (CEL). Studies hitherto have mostly related to advanced glycation end products of fluorescent substances, such as pentosidine or argpyrimidine.

Thus, the present inventors isolated and identified a novel strain that can effectively inhibit the production of nonfluorescent advanced glycation end products while studying to find a novel material that can effectively inhibit nonfluorescent advanced glycation end products, and the present inventors confirmed that these strains have the activity of inhibiting nonfluorescent advanced glycation end products.

As a novel strain having the activity of inhibiting the production of advanced glycation end products, which was isolated and identified in the present invention, the present inventors isolated and identified a *Lactococcus lactis* KF140 strain and deposited it at the Korean Culture Center of Microorganisms (KCCM), which is an international depositary authority, and an accession number KCCM 11673P was assigned; isolated and identified a *Bacillus subtilis* KF11 strain and deposited it on Feb. 24, 2017, at the Korean Culture Center of Microorganisms (KCCM), which is an international depositary authority, and an accession number KCCM 11981P was assigned; isolated and identified a *Lactobacillus paracasei* KF00816 strain and deposited it on Mar. 24, 2017, at the Korean Culture Center of Microorganisms (KCCM), which is an international depositary authority, and an accession number KCCM 11998P was assigned; isolated and identified a *Lactobacillus pentosus* KF8 strain and deposited it on Mar. 24, 2017, at the Korean Culture Center of Microorganisms (KCCM), which is an international depositary authority, and an accession number KCCM 11997P was assigned.

Furthermore, in order to analyze the activity of reducing advanced glycation end products of the novel strains isolated and identified in the present invention, the present inventors treated the samples containing advanced glycation end products with each of the novel strains of the present invention and the comparison strains, and then, measured the content of advanced glycation end products in the culture medium. The result indicated that the novel strains of the present invention showed the remarkably better effect of reducing advanced glycation end products, compared to the conventional strains belonging to the same genus and the commercially available probiotic products.

Furthermore, the present inventors revalidated the effect of reducing advanced glycation end products of the above strain through the animal experiments, wherein the food highly containing CML, one of nonfluorescent advanced glycation end products, was prepared, 6-week-old male mice ingested it, and the CML concentration in blood was measured in subject of in the group ingesting the novel strain identified in the present invention and the group not ingesting the novel strain.

The result confirmed that the content of CML in blood was remarkably reduced in the group ingesting each of a *Lactococcus lactis* KF140 (accession number KCCM11673P) strain, a *Bacillus subtilis* KF11 (accession number KCCM11981P) strain, a *Lactobacillus pentosus* KF8 (accession number KCCM11997P) strain, or a *Lactobacillus paracasei* KF00816 (accession number KCCM11998P) strain, which is the novel strain of the present invention, compared to the group not ingesting the novel strain.

Thus, the present inventors found that the novel strains isolated and identified in the present invention can be usefully utilized to prepare various products for reducing advanced glycation end products.

Therefore, the present invention may provide a *Lactococcus lactis* KF140 (accession number KCCM11673P) strain, a *Bacillus subtilis* KF11 (accession number KCCM11981P) strain, a *Lactobacillus pentosus* KF8 (accession number KCCM11997P) strain, or a *Lactobacillus paracasei* KF00816 (accession number KCCM11998P) strain, which is the novel strain. In addition, the present invention may provide a food composition having the activity of reducing advanced glycation end products, comprising the novel strain of the present invention, a lysate thereof, or a culture thereof as an active ingredient.

In the present invention, the advanced glycation end products described above are nonfluorescent advanced glycation end products, wherein the nonfluorescent advanced glycation end products may include N-carboxymethyl lysine (CML) or N-carboxyethyl lysine (CEL).

The food composition of the present invention includes all forms of functional food, nutritional supplement, health food, food additives, etc. The food composition of the above type may be manufactured in various forms according to the conventional methods known in the art. For example, as a health food, at least one of the group of the novel strain of the present invention itself, a lysate thereof, and a culture of the above strain may be drunken by manufacturing in form of tea, juice, and drink, and may be ingested by granulation, encapsulation, and pulverization. In addition, at least one of the group of the novel strain of the present invention, a lysate thereof, and a culture thereof may be manufactured in form of a composition by mixing with a known substance or an active ingredient known to have the effect of reducing advanced glycation end products. In addition, a functional food may be manufactured by adding at least one of the group of the novel strain of the present invention, a lysate thereof, and a culture thereof to beverages (including alcoholic beverages), fruits and their processed foods (for example, a canned fruit, a bottled fruit, jam, marmalade, etc.), fish, meat, and its processed food (for example, ham, sausage corned beef, etc.), breads and noodles (for example, udon, buckwheat noodle, ramen, spaghetti, macaroni, etc.), fruit juice, various drinks, cookies, taffy, dairy products (for example, butter, cheese, etc.), edible vegetable oil and fat, margarine, vegetable protein, retort food, frozen food, various seasonings (for example, bean paste, soy sauce, sauce, etc.), etc.

The preferable content of the novel strain of the present invention, a lysate thereof, and a culture thereof, etc. in the food composition of the present invention is 0.01 to 50 wt % in a finally manufactured food, but not limited thereto. In addition, in order to use in form of food additives, at least one selected from the group consisting of the novel strain of the present invention, a lysate thereof, and a culture thereof as an active ingredient may be manufactured in form of powder or concentrate.

In addition, the present invention may provide a pharmaceutical composition for preventing or treating a disease caused by advanced glycation end products, comprising a *Lactococcus lactis* KF140 (accession number KCCM11673P) strain, a *Bacillus subtilis* KF11 (accession number KCCM11981P) strain, a *Lactobacillus pentosus* KF8 (accession number KCCM11997P) strain, or a *Lactobacillus paracasei* KF00816 (accession number KCCM11998P) strain, which are the novel strains of the present invention; a lysate thereof; or a culture thereof as an active ingredient, wherein the above disease may include, but is not limited to, diabetes, chronic kidney disease, heart disease, vascular disease, diabetic retinopathy, diabetic neuropathy, diabetic cataract, and diabetic nephropathy.

With regard to the diabetic retinopathy described above, according to the reported research result, in case of diabetic retinopathy, it has been found that the CML expression level increases higher than the normal level when comparing the CML level of diabetic retinopathy patients and the CML level of normal people, and CML may be targeted for therapeutic agents of diabetic retinopathy. It is reported that diabetic retinopathy can be treated by inhibiting CML.

In addition, it has been known that the CML level of diabetic cataract patients increases higher than the CML level of non-diabetic cataract patients. It has been found that CML is a main cause of diabetic cataract. The CML level increases when a diabetic nephropathy disease occurs. Thus, it has been known that CML is a factor causing a diabetic nephropathy disease.

In addition, it has been found that the CML level more increases, compared to the normal level, when chronic kidney disease occurs. Thus, it has been known that the increased CML level may be used as a factor indicating an occurrence of chronic kidney disease, and the CML inhibitor may be a therapeutic agent of chronic kidney disease.

Furthermore, it has been known that CML is a risk factor of diabetic neuropathy. In the research result, it is reported that the CML level of diabetic neuropathy patients remarkably increases as compared to the CML level of normal patients.

In case of vascular disease, the CML level also increases when vascular disease occurs, and thus, it has been known that CML is a risk factor of vascular disease, and it has been known that vascular disease may be prevented or treated by inhibiting CML. It has been known that CML is a main cause of heart disease and diabetes, and the CML level increases when these diseases occur.

Therefore, such diseases may be treated by inhibiting nonfluorescent advanced glycation end products, such as CML.

The pharmaceutical composition of the present invention may contain a pharmaceutically acceptable salt alone, or may further contain at least one pharmaceutically acceptable carrier, excipient, or diluent. A pharmaceutically acceptable carrier may include, for example, a carrier for oral administration or a carrier for parenteral administration. A carrier for oral administration may include lactose, starch, cellulose derivatives, magnesium stearate, stearic acid, etc. In addition, a carrier for parenteral administration may include water, suitable oil, saline, aqueous glucose, glycol, etc., and may further include a stabilizer and a preservative. A suitable stabilizer includes an antioxidant, such as sodium hydrogen sulfite, sodium sulfite, or ascorbic acid. A suitable preservative includes benzalkonium chloride, methyl- or propyl-paraben, and chlorobutanol. Other pharmaceutically acceptable carrier may be referred to the described in the following literature (Remington's Pharmaceutical Sciences, 19th ed., Mack Publishing Company, Easton, PA, 1995).

The pharmaceutical composition of the present invention may be administered by any method to a mammal including a human. For example, it may be administered orally or parenterally. A parenteral administration method includes, but is not limited to, intravenous, intramuscular, intraarterial, intramedullary, intrathecal, intracardiac, transdermal, subcutaneous, intraperitoneal, intranasal, intestinal, topical, sublingual, or intracolonic administration. Preferably, the pharmaceutical composition of the present invention may be administered orally or transdermally.

The pharmaceutical composition of the present invention may be formulated in a formulation for oral administration or a formulation for parenteral administration by the administration routes as described above.

In case of a formulation for oral administration, the composition of the present invention may be formulated using the methods known in the art into powder, granules, tablets, pills, sugar-coated tablets, capsules, liquids, gels, syrups, slurries, suspensions, etc. For example, a formulation for oral administration may be obtained as tablets or dragees by blending an active ingredient with a solid excipient, milling them, adding a suitable adjuvant, and then processing into a granule mixture. Examples of suitable excipients may include sugars, such as lactose, dextrose, sucrose, sorbitol, mannitol, xylitol, erythritol, maltitol, etc., starches, such as corn starch, wheat starch, rice starch, potato starch, etc., celluloses, such as cellulose, methyl cellulose, sodium carboxymethylcellulose, hydroxypropylmethylcellulose, etc., fillers, such as gelatin, polyvinylpyrrolidone, etc. In addition, in some cases, cross-linked polyvinylpyrrolidone, agar, alginic acid, sodium alginate, etc. may be added as a disintegrant. Furthermore, the pharmaceutical composition of the present invention may further comprise anticoagulants, lubricants, wetting agents, flavoring agents, emulsifiers, antiseptics, etc.

The formulation for parenteral administration may be formulated in the form of injections, creams, lotions, external ointments, oils, moisturizers, gels, aerosols, and nasal inhalers using the methods known in the art. These formulations are described in the literature (Remington's Pharmaceutical Science, 15th Edition, 1975. Mack Publishing Company, Easton, Pennsylvania 18042, Chapter 87: Blaug, Seymour), which is a formulary generally known to all pharmaceuticals and chemistry.

The total effective amount of the novel strain of the present invention itself, a lysate thereof, and a culture of the above strain, etc., may be administered to a patient as a single dose, and may be administered by fractionated treatment protocol, that is a long-term administration of multiple doses. The pharmaceutical composition of the present invention may vary the content of the active ingredient, depending on the severity of the disease. The preferable total dose of the strain of the present invention, a lysate thereof and a culture thereof may be about 0.01 ug to 1,000 mg, most preferably 0.1 ug to 100 mg per 1 kg of patient's body weight per day. However, the dose of the strain of the present invention itself, a lysate thereof, and a culture of the above strain, etc., is determined upon consideration of, various factors, such as patient's age, weight, health condition, sex, severity of diseases, diet, excretion rate, etc. as well as administration routes of the pharmaceutical composition and the number of times being treated, for determining the effective dosage for the patient. Thus, upon consideration of such aspects, a person having ordinary skill in the art would be able to determine an appropriate effective dosage according to the certain use of the strain of the present invention, a lysate thereof, and a culture thereof as an immune system enhancer. The pharmaceutical composition according to the present invention is not particularly limited to the formulations, administration routes, and administration methods as long as the effect of the present invention shows.

In addition, the present invention provides a composition for intestinal regulation, a probiotic composition, a feed composition, comprising at least one selected from the group consisting of the novel strain, a lysate thereof, and a culture thereof as an active ingredient. The novel strain of the present invention is a strain having the activity of reducing advanced glycation end products, and thus, it may be used for the health enhancement of humans and animals, i.e., as a composition for intestinal regulation, a probiotic composition, or a feed composition. The above composition may comprise the above strain itself, a lysate thereof, and a culture of the above strain, etc., as an active ingredient, and may further comprise an excipient or a carrier. The above composition includes a culture medium itself cultured in a liquid medium, a filtrate (centrifuged supernatant), wherein a strain is removed by filtration or centrifugation of the above culture medium, etc. The content of the strain of the present invention in the composition may vary depending on the use and formulation of the composition.

The composition for intestinal regulation or the probiotic composition according to the present invention may be prepared and administered in various formulations and methods. For example, the novel strain of the present invention, a lysate thereof, and a culture thereof may be prepared and administered in form of tablets, troches, capsules, elixirs, syrups, powder, suspensions, granules, etc. by mixing with carriers and flavoring agents conventionally used in the pharmaceutical field.

Binders, glidants, disintegrants, excipients, solubilizers, dispersants, stabilizers, suspending agents, etc. may be used as a carrier. The administration manner may use the oral, parenteral, or application method, and oral administration is preferred. In addition, the dosage may be appropriately selected, depending on the absorption rate, the inactivation rate, and the excretion speed of the active ingredient in the body, the administered person's age, sex, condition, etc. In addition, the feed composition according to the present invention may be prepared in form of a fermented feed, a formula feed, a pellet form, a silage, etc.

The above fermented feed may be prepared by fermenting the organic material by adding the novel strain of the present invention and various microbial strains or enzymes, and the above formula feed may be prepared by mixing the strain of the present invention with various kinds of a regular feed. The feed in pellet form may be prepared by formulating the above fermented feed or the formula feed with pelletizer, and the silage may be prepared by fermenting the green fodder with the strain according to the present invention.

In addition, the present invention provides a fermented product comprising at least one selected from the group consisting of the novel strain of the present invention, a lysate thereof, and a culture thereof as an active ingredient. The preparation method of the fermented product typically consists of the steps of the preparation of the raw material, the addition of lactic acid bacteria, fermentation, recovery of the finished product, etc. The step of the preparation of the raw material is a step of the preparation of a material which is subject to fermentation, and the preparation of the fermentation conditions such that the fermentation is well performed. The addition of lactic acid bacteria is the addition of a suitable amount of bacteria in accordance with the amount of the fermentation subject, wherein in the present invention, it is characterized in that the novel strain of the present invention is used. The fermentation is to be performed according to the conventional fermentation conditions of fermentation bacteria, wherein it is performed preferably at 37° C. to 43° C. for 4 to 168 hours. The recovery of the finished product includes all customary work-up processes for facilitating storage, transportation, packaging, etc., as well as removing the undesirable by-products or the unfermented materials from the ferments. The fermented product prepared following the method described above may be preferably a beverage, wherein the beverage refers to, for example, the product prepared by culturing the strain of the present invention to subject it to be lactic acid fermented, diluting it by adding sterilized water thereto, adding sugars, flavoring agents, etc., and then, filling a container therewith. Because the beverage usually contains lactic acid bacteria that are alive, the activity of controlling intestinal functions in intestine after drinking can be expected.

Furthermore, the present invention can provide a method for inhibiting advanced glycation end products, by using the novel strain of the present invention, a lysate thereof, or a culture thereof. The above method according to the present invention may include the steps of treating a sample containing advanced glycation end products with the novel strain of the present invention, a lysate thereof, or a culture thereof, wherein the content of advanced glycation end products of the above sample may be reduced through the steps.

In addition, the above method can include the steps of administering the novel strain of the present invention, a lysate thereof, or a culture thereof to a subject in need thereof, wherein the above subject may be a mammal including a human.

In one embodiment of the present invention, the content of advanced glycation end products in the mouse serum can be reduced by feeding a diet containing the novel strain of the present invention to a mouse.

Embodiment for Working the Invention

Hereafter, the present invention will be described in further detail with reference to the following examples. It is intended that these examples illustrate the present invention in more detail and the scope of the present invention is not limited to these examples.

Example 1

Isolation and Identification of a Novel Strain Having the Activity of Reducing Advanced Glycation End Products <1-1> Isolation and Identification of a *Lactococcus lactis* KF140, a Novel Strain The present inventors performed the following experiments in order to isolate the novel strain having the activity of reducing advanced glycation end products from kimchi. Kimchi was suspended in 0.85% physiological saline, a part of suspension was plated on a MRS solid medium, and then, it was cultured at 37° C. The colonies formed after culturing were taken, they were streak-cultured in a MRS medium, and the pure single colonies uncontaminated were obtained. The sequencing analysis was performed after isolating 16S rDNA from the obtained strain.

As a result of sequencing analysis, since the base sequence of 16s rDNA of the above strain showed a homology of 99% with the conventional *Lactococcus lactis* NCDO604 (T) strain, the strain identified in the present invention was found to be a strain belonging to a *Lactococcus lactis*, wherein the base sequence of 16s rDNA was shown in SEQ ID NO: 1. Thereafter, the isolated strain was cultured using a MRS medium, wherein the culture condition was pH 6.5±0.2, temperature 37° C., and 48 hours stationary culture, and oxygen requirement was facultative anaerobe, the strain was preserved through the freeze-drying preservation or cell suspension freezing. Thereafter, the present inventors designated the isolated strain as a *Lactococcus lactis* KF140, which was deposited with the Korean Culture Center of Microorganisms (KCCM), an international depositary authority, and an accession number KCCM 11673P was given.

<1-2> Isolation and Identification of a *Bacillus subtilis* KF11, a Novel Strain The following experiments were performed in order to isolate the novel strain having the activity of reducing advanced glycation end products from bean paste. The bean paste was suspended in 0.85% physiological saline, a part of suspension was plated on a TSB solid medium, and then, it was cultured at 37° C. The colonies formed after culturing were taken, they were streak-cultured in a TSB medium, and the pure single colonies uncontaminated were obtained. The sequencing analysis was performed after isolating 16S rDNA from the obtained strain.

As a result of sequencing analysis, since the base sequence of 16s rDNA of the above strain showed a homology of 99% with the conventional *Bacillus subtilis* KCTC 13429 (T) strain, the strain identified in the present invention was found to be a strain belonging to a *Bacillus subtilis*, wherein the base sequence of 16s rDNA was shown in SEQ ID NO: 2. Thereafter, the isolated strain was cultured using a TSB medium under the culture condition of pH 7.0±0.2, temperature 37° C., and 24 hours with stirring, oxygen requirement was facultative anaerobe, and the strain was preserved through the freeze-drying preservation or cell suspension freezing.

Thereafter, the present inventors designated the isolated strain as a *Bacillus subtilis* KF11, which was deposited with the Korean Culture Center of Microorganisms (KCCM), an international depositary authority, on Feb. 24, 2017, and an accession number KCCM 11981P was given.

<1-3> Isolation and Identification of a *Lactobacillus paracasei* KF00816

A *Lactobacillus paracasei* KF00816 strain was isolated from kimchi and identified, wherein the kimchi prepared in a traditional way was suspended in 0.85% physiological saline, a part of suspension was plated on a MRS solid medium, and then, it was cultured at 37° C. The colonies formed after culturing were taken, they were streak-cultured in a MRS medium, and the pure single colonies uncontaminated were obtained. The sequencing analysis was performed after isolating 16S rDNA from the obtained strain.

As a result of analysis, since the base sequence of 16s rDNA of the above strain showed a homology of 99% with the conventional *Lactobacillus paracasei* ATCC 25302 (T), the strain identified in the present invention was found to be a strain belonging to a *Lactobacillus paracasei*, wherein the analyzed base sequence of 16s rDNA was shown in SEQ ID NO: 3. Thereafter, the isolated strain was cultured using a MRS medium, wherein the culture condition was pH 6.5±0.2, temperature 37° C., and 48 hours stationary culture, oxygen requirement was facultative anaerobe, and the strain was preserved through the freeze-drying preservation or cell suspension freezing.

Thereafter, the present inventors designated the isolated strain as a *Lactobacillus paracasei* KF00816, which was deposited with the Korean Culture Center of Microorganisms (KCCM), an international depositary authority, on Mar. 24, 2017, and an accession number KCCM 11998P was given.

<1-4> Isolation and Identification of a *Lactobacillus pentosus* KF8 Strain

A *Lactobacillus pentosus* KF8 strain having the activity of reducing advanced glycation end products was isolated from a traditional soy sauce, wherein the traditional soy sauce was suspended in 0.85% physiological saline, a part of suspension was plated on a MRS solid medium, and then, it was cultured at 37° C. The colonies formed after culturing were taken, they were streak-cultured in a MRS medium, and the pure single colonies uncontaminated were obtained. The sequencing analysis was performed after isolating 16S rDNA from the obtained strain.

As a result of sequencing analysis, since the base sequence of 16s rDNA of the above strain showed a homology of 97% with the conventional *Lactobacillus pentosus* DSM 20314 (T), the strain identified in the present invention was found to be a strain belonging to a *Lactobacillus pentosus*, wherein the analyzed base sequence of 16s rDNA was shown in SEQ ID NO: 4. Thereafter, the isolated strain was cultured using a MRS medium, wherein the culture condition was pH 6.5±0.2, temperature 37° C., and 48 hours stationary culture, oxygen requirement was facultative anaerobe, and the strain was preserved through the freeze-drying preservation or cell suspension freezing.

Thereafter, the present inventors designated the isolated strain as a *Lactobacillus pentosus* KF8, which was deposited with the Korean Culture Center of Microorganisms (KCCM), an international depositary authority, on Mar. 24, 2017, and an accession number KCCM 11997P was given.

Example 2

Analysis of the Efficacy of Reducing Advanced Glycation End Products of the Novel Strains of the Present Invention In order to analyze whether each of four novel strains isolated and identified in Example 1 described above has the efficacy of reducing advanced glycation end products, the present inventors confirmed the degree of the activity of reducing advanced glycation end products contained in milk by the following methods.

<2-1> Preparation of a Food Containing Advanced Glycation End Products

The CML-containing food was prepared in order to analyze whether the novel strains of the present invention have the activity of reducing a CML ($N^\varepsilon$-(Carboxymethyl)-L-lysine), a kind of nonfluorescent advanced glycation end products. That is, casein, a milk protein, and lactose, a milk sugar, were used in order to reduce the CML produced during the process of heat treatment of milk, wherein sodium caseinate and D-lactose were purchased from ES FOOD and Sigma-Aldrich, respectively. Upon consideration of a ratio of casein to lactose in milk, a milk protein (casein) and a milk sugar (lactose) were mixed in a ratio of 1:7 and reacted at the temperature of 140° C. for 80 minutes, and it was used to determine the CML-reducing efficacy of the novel strain of the present invention. Wherein, the CML content by Maillard reaction of casein and lactose was found to be 8.24 ug/mL.

<2-2> Strain Used to Analyze the CML-Reducing Activity

The CML-reducing efficacy of the novel strain according to the present invention was analyzed by using the other strains described in Table 1 below and the commercialized probiotic products as a control group. The other strains used as a control group in Table 1 below were purchased from Traditional Food Microorganism Strain Bank, the Korea Food Research Institute, the probiotic products were used as the commercially available products, wherein the probiotic products were shown in FIG. 1. In addition, the media for culturing the strains used in the experiment below were purchased from Difco, a Lactobacilli MRS agar and a Lactobacilli MRS broth were used to culture lactic acid bacteria strains, and TSA (tryptic soy agar) and TSB (tryptic soy broth) were used as culture media of *Bacillus* genus strains. M9 minimal medium (MB cell) was used in the culture for CML reduction of lactic acid bacteria and *Bacil-* lus bacteria, wherein glucose of 2 g/L, CaCl$_2$) of 0.015 g/L, MgSO$_4$ of 0.5 g/L were added to prepare the M9 medium.

TABLE 1

| Strain | Strain Name | Medium | Temperature |
|---|---|---|---|
| Strain of the present invention | Lactococcus lactis KF140 | MRS | 37° C. |
| Strain of the present invention | Bacillus subtilis KF11 | MRS | 37° C. |
| Control group lactic acid bacteria | Enterococcus faecium KF74216 | MRS | 37° C. |
| | Enterococcus faecium KF825 | MRS | 37° C. |
| | Lactobacillus sk10 | MRS | 37° C. |
| | Lactobacillus brevis KF877 | MRS | 37° C. |
| | Lactobacillus brevis sk1 | MRS | 37° C. |
| | Lactobacillus brevis sk2 | TSA | 37° C. |
| | Bacillus subtilis g12 | TSA | 37° C. |
| Strain of the present invention | Lactobacillus pentosus KF8 | MRS | 37° C. |
| Control group lactic acid bacteria | Lactobacillus pentosus KF448 | MRS | 37° C. |
| | Lactobacillus pentosus KF480 | MRS | 37° C. |
| | Lactobacillus brevis sk2 | MRS | 37° C. |
| | Lactobacillus plantarum subsp. plantarum KF144-1 | MRS | 37° C. |
| Strain of the present invention | Lactobacillus paracasei KF00816 | MRS | 37° C. |
| Control group lactic acid bacteria | Lactobacillus paracasei KF702 | MRS | 37° C. |
| | Lactobacillus brevis sk2 | MRS | 37° C. |
| | Lactobacillus brevis KF877 | MRS | 37° C. |
| | Lactobacillus plantarum subsp. plantarum KF144-1 | MRS | 37° C. |
| Control group commercially available probiotics | DR. PROBA BABY (commercial product-01) | | |
| | LACPIDO PREMIUM (commercial product-02) | | |
| | LACTO-FIT alive lactic acid bacteria GOLD (commercial product-03) | | |
| | ProsLab Family (commercial product-04) | | |
| | Superbiotics (commercial product-06) | | |
| | PROBIOTICS lactic acid bacteria VSL#3 (commercial product-07) | | |
| | STRONG BIOTICS (commercial product-05) | | |

<2-3> Analysis of CML Content

After culturing lactic acid bacteria and the probiotic products of Table 1 above in a culture medium containing CML for 24 hours, the changed amount of NE-(carboxymethyl) lysine (CML) was measured using CML ELISA kit (CircuLex, Ina, Nagano, Japan). The supernatant or standard sample and the anti-CML-adduct monoclonal antibody were added to 96-well pre-coated with CML-BSA, and reacted at room temperature for 1 hour. After washing four times with wash buffer, the HRP conjugated detection antibody of 100 μl was added and reacted for 1 hour and then washed four times with wash buffer, and a substrate-containing solution of 100 μl was added and reacted under the conditions of light protection for 20 minutes, and then, a quiescent solution of 100 μl was added, the absorbance was measured at 450 nm using a microplate reader, and the result was shown in the table below. Wherein, the negative control group (CON; control) in Table 2 below was the group containing CML measured by Maillard reaction of the above <2-1> in content of 8.24 ug/mL, in which lactic acid bacteria was not added, and the result was measured based on the CML content of the negative control group of 100%.

TABLE 2

| Strain | Strain Name | CML content (Unit: % of control) |
|---|---|---|
| Novel strain of the present invention | Lactococcus lactis KF140 | 6.2 |
| | Bacillus subtilis KF11 | 10.6 |
| | Lactobacillus pentosus KF8 | 13.6 |
| | Lactobacillus paracasei KF00816 | 20.2 |
| Negative control group | — | 100 |
| Control group lactic acid bacteria | Enterococcus faecium KF74216 | 76.7 |
| | Enterococcus faecium KF825 | 90.9 |
| | Lactobacillus sk10 | 96.7 |
| | Lactobacillus brevis KF877 | 69.9 |
| | Lactobacillus brevis sk1 | 98.5 |
| | Lactobacillus brevis sk2 | 72.4 |
| | Bacillus subtilis g12 | 63.4 |
| | Lactobacillus pentosus KF448 | 91.1 |
| | Lactobacillus pentosus KF480 | 76.7 |
| | Lactobacillus brevis sk2 | 72.4 |
| | Lactobacillus plantarum subsp. plantarum KF144-1 | 93.0 |
| | Lactobacillus paracasei KF702 | 88.4 |
| | Lactobacillus brevis sk2 | 72.4 |
| | Lactobacillus brevis KF877 | 69.9 |
| | Lactobacillus plantarum subsp. plantarum KF144-1 | 93.0 |
| Control group commercially available probiotics | DR. PROBA BABY (commercial product-01) | 102.0 |
| | LACPIDO PREMIUM (commercial product-02) | 67.2 |
| | LACTO-FIT alive lactic acid bacteria GOLD (commercial product-03) | 86.0 |
| | ProsLab Family (commercial product-04) | 80.9 |
| | Superbiotics (commercial product-06) | 106.1 |
| | PROBIOTICS lactic acid bacteria VSL#3 (commercial product-07) | 104.9 |
| | STRONG BIOTICS (commercial product-05) | 100.9 |

As a result of analysis, based on the Maillard reaction product of casein and lactose containing CML in a concentration of 8.24 ug/mL, which was prepared to analyze the CML-reducing efficacy in Example <2-1> above, each of lactic acid bacteria of the above Table 1 and FIG. 1 was inoculated in the culture medium, and then, the CML content was measured. The result indicated the CML content was remarkably reduced in the groups inoculated with the novel strains of the present invention compared to the other control groups. This result may be also found through the result of FIG. 2 to FIG. 6.

Example 3

Verification of the Efficacy of Reducing Advanced Glycation End Products of the Novel Strains According to the Present Invention Using CML Standard Form Through the result of Example above, the present inventors confirmed that the novel strains of the present invention had the remarkably excellent efficacy of reducing CML compared to the conventional strains and the commercial products having the activity of reducing CML. Accordingly, in order to revalidate the efficacy of reducing CML, NE-(1-carboxymethyl)-L-lysine (CAS: 5746-04-3), which is the most representative nonfluorescent advanced glycation end product among advanced glycation end products, was purchased from Santa Cruz Biotechnology, and its reducing activity was analyzed once again. The CML standard form of a purity of 99% was used, and the CML reducing analysis was analyzed in the same manner as in Example 2 above.

Figure 7:
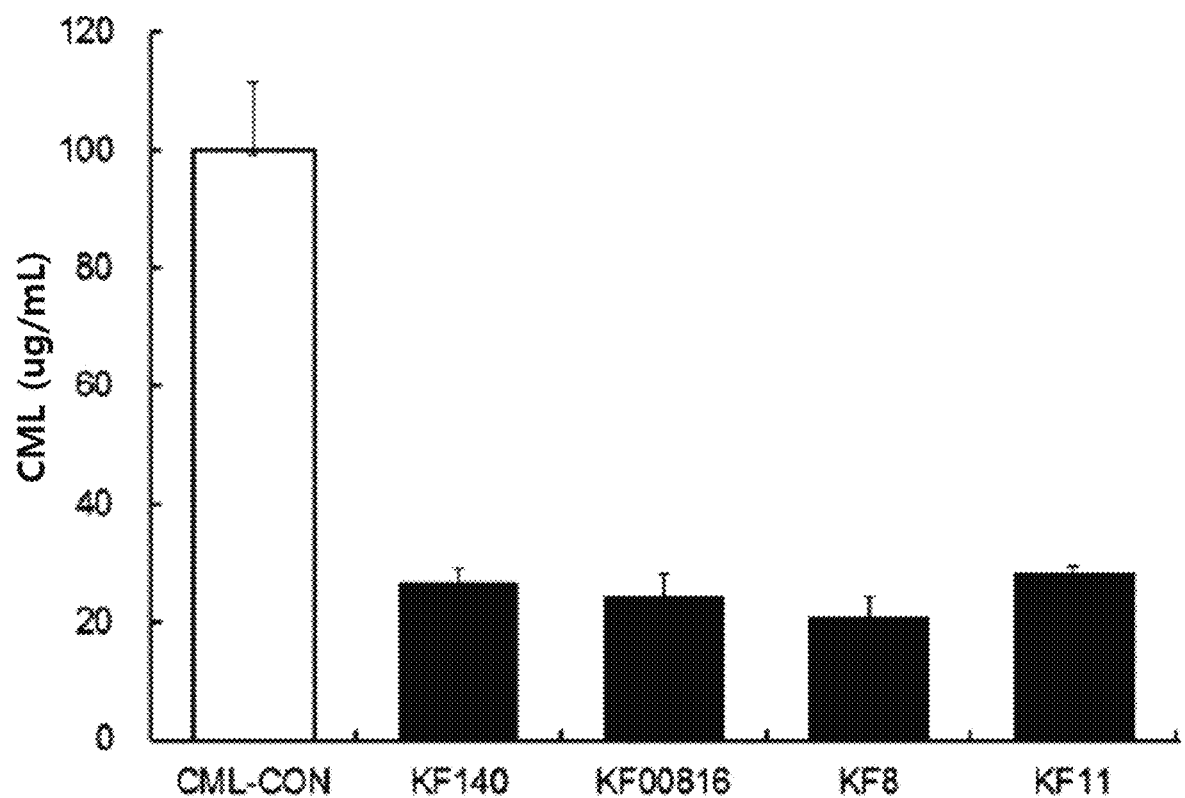
FIG. 7 shows the result of comparative analysis of the activity of reducing CML for the CML standard form and the novel strains isolated and identified in the present invention.

The analysis result, as shown in FIG. 7, indicated that the CML content of 100 percent was remarkably inhibited by treatment of the novel strains of the present invention, in particular, a *Lactococcus lactis* KF140 strain was shown to have the CML-reducing activity of about 73%, a *Bacillus subtilis* KF11 strain was shown to have the high CML-reducing activity of about 72%, a *Lactobacillus paracasei* KF00816 strain was shown to have the high CML-reducing activity of about 75.4%, and a *Lactobacillus pentosus* KF8 strain was shown to have the high CML-reducing activity of about 80%. Therefore, through this result, the present inventors reconfirmed that the above novel strains isolated and identified in the present invention had the excellent activity of reducing CML.

Example 4

Analysis of the Efficacy of Reducing CML in Blood of the Novel Strains of the Present Invention Through the Animal Experiments Furthermore, the present inventors performed the experiments to determine whether to directly reduce the CML content in blood when using the novel strains of the present invention through the animal experiments. To this end, the high-CML food by Maillard reaction of casein, a protein ingredient included in milk, and lactose, a sugar ingredient included in milk, was prepared by the method described in the above example, it was ingested by SD mice (6-week-old, male), and then, the change of the CML content in blood was confirmed, wherein each of the novel strains of the present invention was ingested in amount of 50 mg/kg for one week, the high-CML food was ingested by 12-hour fasted mice, and then after 8 hours, the CML concentration in blood was measured. In addition, the group that ingested the high-CML food only and did not ingest the novel strains of the present invention was used as the negative control group.

TABLE 3

Result of measuring the CML content in blood of mice

| Experiment Group | CML content (%) average |
| --- | --- |
| Normal diet ingestion group (Nor) | 100.00 |
| High-CML food ingestion group (CML) | 230.13 |
| KF140 novel strain ingestion group | 155.58 |
| KF00816 novel strain ingestion group | 179.35 |
| KF8 novel strain ingestion group | 87.11 |
| KF11 novel strain ingestion group | 56.27 |

Figure 8:
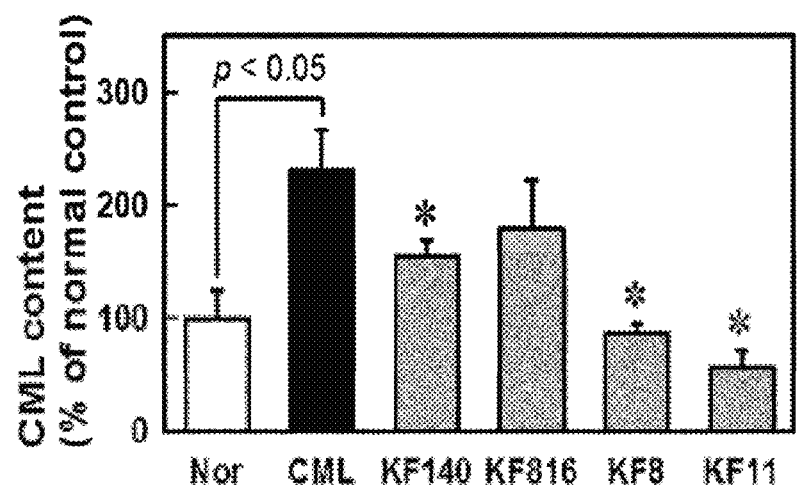
FIG. 8 shows the result of analysis of the effect of reducing CML in blood according to the ingestion of the novel strain of the present invention, wherein mice ingesting a high-CML food are used as a subject.

The analysis result, as shown in Table 3 above and FIG. 8, confirmed that the CML concentration in blood was shown to increase by 2.3 times on an average in the mouse group that ingested the high-CML food only compared to the experiment group that did not ingest the high-CML food, whereas the CML content in blood increased by the high-CML food ingestion was effectively reduced in the group that ingested KF140, KF00816, KF8, and KF11, the novel strains of the present invention.

As presented in the above results, the present inventors confirmed that a *Lactococcus lactis* KF140 strain, the novel strain isolated and identified in the present invention had the activity of effectively reducing advanced glycation end products, and thus, the present inventors found that the strain could be usefully used in the preparation of the pharmaceutical products and the functional food against various diseases caused by advanced glycation end products.

As described above, the present invention has been described mainly based upon the preferable examples. A person having ordinary skill in the art would be able to understand that the present invention may be implemented in a modified form within the scope which does not deviate from the essential characteristics of the present invention. Therefore, the examples shown above should be considered from an explanatory point of view, not a limited point of view. The scope of the present invention is defined by the claims, not the foregoing description, and all of the differences within the scope equivalent thereto should be interpreted to be included in the scope of the present invention.

The present patent is a result of a task corresponding to task identification number E0164401-03, ministry name: Ministry of Science and ICT, research management professional agency: Korea Food Research Institute, managing department: Korea Food Research Institute, research project name: Korea Food Research Institute main project, research task title: analysis of main onset factor of diabetes complications and technical development of their reduction, research period: Jan. 1, 2016 to Dec. 31, 2018; and a task corresponding to task identification number E0170601-02, ministry name: Ministry of Science and ICT, research management professional agency: Korea Food Research Institute, managing department: Korea Food Research Institute, research project name: Korea Food Research Institute main project, research task title: food and drug research of improvement of intestinal microorganism-mediated metabolic disease, research period: Jan. 1, 2017 to Dec. 31, 2025, which have been conducted as a part of the national research task project.

[Accession number]
Depositary authority name: Korean Culture Center of Microorganisms (foreign country)
Accession number: KCCM11997P
Deposit date: Mar. 24, 2017
Depositary authority name: Korean Culture Center of Microorganisms (foreign country)
Accession number: KCCM11998P
Deposit date: Mar. 24, 2017
Depositary authority name: Korean Culture Center of Microorganisms (foreign country)
Accession number: KCCM11673P
Deposit date: Mar. 6, 2015
Depositary authority name: Korean Culture Center of Microorganisms (foreign country)
Accession number: KCCM11981P
Deposit date: Feb. 24, 2017

The invention claimed is:

1. A method for inhibiting advanced glycation end products (AGEs), the method comprising administering a novel strain, a lysate thereof, or a culture thereof to a subject in need thereof,
wherein the novel strain has the activity of reducing advanced glycation end products, wherein the novel strain is a *Lactococcus lactis* KF140 (accession number KCCM11673P) strain.

2. The method of claim 1, wherein the novel strain, a lysate thereof, or a culture thereof is provided in a composition comprising a food composition, a pharmaceutical composition, a composition for intestinal regulation, a probiotic composition, a feed composition or a fermented product-containing composition.

3. The method of claim 2, wherein the food composition improves diabetes, chronic kidney disease, heart disease, vascular disease, diabetic retinopathy, diabetic neuropathy, diabetic cataract, or diabetic nephropathy, which are caused by advanced glycation end products.

4. The method of claim 2, wherein the pharmaceutical composition treats a disease related to advanced glycation end products, wherein the disease is selected from the group consisting of diabetes, chronic kidney disease, heart disease, vascular disease, diabetic retinopathy, diabetic neuropathy, diabetic cataract, and diabetic nephropathy.

5. The method of claim 1, wherein the method improves a disease selected from diabetes, chronic kidney disease, heart disease, vascular disease, diabetic retinopathy, diabetic neuropathy, diabetic cataract, or diabetic nephropathy, in a patient in need thereof.

6. The method of claim 1, wherein the AGEs are non-fluorescent advanced glycation end products.

7. A method of reducing $N^{\varepsilon}$-(carboxymethyl) lysine (CML), the method comprising administering a novel strain, a lysate thereof, or a culture thereof to a subject in need thereof,
wherein the novel strain has the activity of reducing $N^{\varepsilon}$-(carboxymethyl) lysine (CML), wherein the novel strain is a *Lactococcus lactis* KF140 (accession number KCCM11673P) strain.

8. The method of claim 7, wherein the method improves a disease selected from diabetes, chronic kidney disease, heart disease, vascular disease, diabetic retinopathy, diabetic neuropathy, diabetic cataract, or diabetic nephropathy, in a patient in need thereof.

* * * * *

SEQUENCE LISTING

<160> NUMBER OF SEQ ID NOS: 4

<210> SEQ ID NO 1
<211> LENGTH: 1490
<212> TYPE: DNA

<213> ORGANISM: Artificial Sequence
<220> FEATURE:
<223> OTHER INFORMATION: Lactococcus lactis KF140 16s rDNA sequence

<400> SEQUENCE: 1

```
tgatcatggc tcaggacgaa cgctggcggc gtgcctaata catgcaagtt gagcgctgaa     60
ggttggtact tgtaccgact ggatgagcag cgaacgggtg agtaacgcgt ggggaatctg    120
cctttgagcg ggggacaaca tttggaaacg aatgctaata ccgcataaaa actttaaaca    180
caagttttaa gtttgaaaga tgcaattgca tcactcaaag atgatcccgc gttgtattag    240
ctagttggtg aggtaaaggc tcaccaaggc gatgatacat agccgacctg agagggtgat    300
cggccacatt gggactgaga cacggcccaa actcctacgg gaggcagcag tagggaatct    360
tcggcaatgg acgaaagtct gaccgagcaa cgccgcgtga gtgaagaagg ttttcggatc    420
gtaaaactct gttggtagag aagaacgttg gtgagagtgg aaagctcatc aagtgacggt    480
aactacccag aaagggacgg ctaactacgt gccagcagcc gcggtaatac gtaggtcccg    540
agcgttgtcg ggatttattg ggcgtaaagc gagcgcaggg ggtttattaa gtctggtgta    600
aaaggcagtg gctcaaccat tgtatgcatt ggaaactggt agacttgagt gcaggagagg    660
agagtggaat tccatgtgta gcggtgaaat gcgtagatat atggaggaac accggtggcg    720
aaagcggctc tctggcctgt aactgacact gaggctcgaa agcgtgggga gcaaacagga    780
ttagataccc tggtagtcca cgccgtaaac gatgagtgct agatgtaggg agctataagt    840
tctctgtatc gcagctaacg caataagcac tccgcctggg gagtacgacc gcaaggttga    900
aactcaaagg aattgacggg ggcccgcaca agcggtggag catgtggttt aattcgaagc    960
aacgcgaaga accttaccag gtcttgacat actcgtgcta ttcctagaga taggaagttc   1020
cttcgggaca cgggatacag gtggtgcatg gttgtcgtca gctcgtgtcg tgagatgttg   1080
ggttaagtcc cgcaacgagc gcaaccccta tgttagttg ccatcattaa gttgggcact   1140
ctaacgagac tgccggtgat aaaccggagg aaggtgggga tgacgtcaaa tcatcatgcc   1200
ccttatgacc tgggctacac acgtgctaca atggatggta caacgagtcg cgagacagtg   1260
atgtttagct aatctcttaa aaccattctc agttcggatt gtaggctgca actcgcctac   1320
atgaagtcgg aatcgctagt aatcgcggat cacacgccgc ggggttgaat acgttcccgg   1380
gccttgtaca caccgcccgt cacaccacgg gagttgggag tacccgaagt atgttgccta   1440
accgcaaagg agggcgcttc ctaaagtaag accgatgact gggggtgaag                1490
```

<210> SEQ ID NO 2
<211> LENGTH: 1459
<212> TYPE: DNA
<213> ORGANISM: Artificial Sequence
<220> FEATURE:
<223> OTHER INFORMATION: Bacillus subtilis KF11 16s rDNA sequence

<400> SEQUENCE: 2

```
accccaatca tctgtcccac cttcggcggc tggctcctaa aaggttacct caccgacttc     60
gggtgttaca aactctcgtg gtgtgacggg cggtgtgtac aaggcccggg aacgtattca    120
ccgcggcatg ctgatccgcg attactagcg attccagctt cacgcagtcg agttgcagac    180
tgcgatccga actgagaaca gatttgtggg attggcttaa cctcgcggtt tcgctgccct    240
ttgttctgtc cattgtagca cgtgtgtagc ccaggtcata agggcatga tgatttgacg    300
tcatccccac cttcctccgg tttgtcaccg gcagtcacct tagagtgccc aactgaatgc    360
tggcaactaa gatcaagggt tgcgctcgtt gcgggactta acccaacatc tcacgacacg    420
```

| | |
|---|---|
| agctgacgac aaccatgcac cacctgtcac tctgccccccg aagggggacgt cctatctcta | 480 |
| ggattgtcag aggatgtcaa gacctggtaa ggttcttcgc gttgcttcga attaaaccac | 540 |
| atgctccacc gcttgtgcgg gcccccgtca attcctttga gtttcagtct tgcgaccgta | 600 |
| ctccccaggc ggagtgctta atgcgttagc tgcagcacta aggggcggaa accccctaac | 660 |
| acttagcact catcgtttac ggcgtggact accagggtat ctaatcctgt tcgctcccca | 720 |
| cgctttcgct cctcagcgtc agttacagac cagagagtcg ccttcgccac tggtgttcct | 780 |
| ccacatctct acgcatttca ccgctacacg tggaattcca ctctcctctt ctgcactcaa | 840 |
| gttccccagt ttccaatgac cctccccggt tgagccgggg gctttcacat cagacttaag | 900 |
| aaaccgcctg cgagccctttt acgcccaata attccggaca acgcttgcca cctacgtatt | 960 |
| accgcggctg ctggcacgta gttagccgtg gctttctggt taggtaccgt caaggtaccg | 1020 |
| ccctattcga acgtacttg ttcttcccta acaacagagc tttacgatcc gaaaaccttc | 1080 |
| atcactcacg cggcgttgct ccgtcagact ttcgtccatt gcggaagatt ccctactgct | 1140 |
| gcctcccgta ggagtctggg ccgtgtctca gtcccagtgt ggccgatcac cctctcaggt | 1200 |
| cggctacgca tcgttgcctt ggtgagccgt tacctcacca actagctaat gcgccgcggg | 1260 |
| tccatctgta agtggtagcc gaagccacct tttatgtttg aaccatgcgg ttcaaacaac | 1320 |
| catccggtat tagcccccggt ttcccggagt tatcccagtc ttacaggcag gttacccacg | 1380 |
| tgttactcac ccgtccgccg ctaacatcag ggagcaagct cccatctgtc cgctcgactt | 1440 |
| gcatgtatta ggcacgccg | 1459 |

```
<210> SEQ ID NO 3
<211> LENGTH: 1500
<212> TYPE: DNA
<213> ORGANISM: Artificial Sequence
<220> FEATURE:
<223> OTHER INFORMATION: lactobacillus paracasei KF00816 16s rDNA
      sequence

<400> SEQUENCE: 3
```

| | |
|---|---|
| gacttcaccc taatcatttg tcccaccttta gacggctcgc tccctaaaag ggttacgcca | 60 |
| ccggcttcgg gtgttacaaa ctctcatggt gtgacgggcg gtgtgtacaa ggcccgggaa | 120 |
| cgtattcacc gcggcgtgct gatccgcgat tactagcgat tccgacttcg tgtaggcgag | 180 |
| ttgcagccta cagtccgaac tgagaatggc tttaagagat tagcttgacc tcgcggtctc | 240 |
| gcaactcgtt gtaccatcca ttgtagcacg tgtgtagccc aggtcataag ggcatgatg | 300 |
| atttgacgtc atccccacct tcctccggtt tgtcaccggc agtcttacta gagtgcccaa | 360 |
| ctaaatgctg gcaactagtc ataagggttg cgctcgttgc gggacttaac ccaacatctc | 420 |
| acgacacgag ctgacgacaa ccatgcacca cctgtcattt tgcccccgaa ggggaaacct | 480 |
| gatctctcag gtgatcaaaa gatgtcaaga cctggtaagg ttcttcgcgt tgcttcgaat | 540 |
| taaaccacat gctccaccgc ttgtgcgggc cccgtcaat tcctttgagt ttcaaccttg | 600 |
| cggtcgtact ccccaggcgg aatgcttaat gcgttagctg cggcactgaa gggcggaaac | 660 |
| cctccaacac ctagcattca tcgtttacgg catggactac cagggtatct aatcctgttc | 720 |
| gctacccatg ctttcgagcc tcagcgtcag ttacagacca gacagccgcc ttcgccactg | 780 |
| gtgttcttcc atatatctac gcatttcacc gctacacatg gagttccact gtcctcttct | 840 |
| gcactcaagt ttcccagttt ccgatgcgct tcctcggtta agccgagggc tttcacatca | 900 |
| gacttaaaaa accgcctgcg ctcgctttac gcccaataaa tccggataac gcttgccacc | 960 |

```
tacgtattac cgcggctgct ggcacgtagt tagccgtggc tttctggttg ataccgtca    1020 cgccgacaac agttactctg ccgaccattc ttctccaaca acagagtttt acgacccgaa   1080
agccttcttc actcacgcgg cgttgctcca tcagacttgc gtccattgtg aagattccc    1140 tactgctgcc tcccgtagga gtttgggccg tgtctcagtc ccaatgtggc cgatcaacct   1200
ctcagttcgg ctacgtatca tcgccttggt gagccattac ctcaccaact agctaatacg   1260
ccgcgggtcc atccaaaagc gatagcttac gccatctttc agccaagaac catgcggttc   1320
ttggatctat gcggtattag catctgtttc caaatgttat cccccactta agggcaggtt   1380
acccacgtgt tactcacccg tccgccactc gttccatgtt gaatctcggt gcaagcaccg   1440
atcatcaacg agaactcgtt cgacttgcat gtattaggca cgccgccagc gttcatccga   1500
```

```
<210> SEQ ID NO 4
<211> LENGTH: 1368
<212> TYPE: DNA
<213> ORGANISM: Artificial Sequence
<220> FEATURE:
<223> OTHER INFORMATION: Lactobacillus pentosus KF8 16s rDNA sequence

<400> SEQUENCE: 4
```

```
cacctggaaa cagatgctaa taccgcataa caacttggac cgcatggtcc gagtttgaaa     60
gatggcttcg gctatcactt ttggatggtc ccgcggcgta ttagctagat ggtggggtaa    120
cggctcacca tggcaatgat acgtagccga cctgagaggg taatcggcca cattgggact    180
gagacacggc ccaaactcct acgggaggca gcagtaggga atcttccaca atggacgaaa    240
gtctgatgga gcaacgccgc gtgagtgaag aagggtttcg gctcgtaaaa ctctgttgtt    300
aaagaagaac atatctgaga gtaactgttc aggtattgac ggtatttaac cagaaagcca    360
cggctaacta cgtgccagca gccgcggtaa tacgtaggtg gcaagcgttg tccggattta    420
ttgggcgtaa agcgagcgca ggcggttttt taagtctgat gtgaaagcct tcggctcaac    480
cgaagaagtg catcggaaac tgggaaactt gagtgcagaa gaggacagtg gaactccatg    540
tgtagcggtg aaatgcgtag atatatggaa gaacaccagt ggcgaaggcg ctgtctggt    600 ctgtaactga cgctgaggct cgaaagtatg ggtagcaaac aggattagat accctggtag    660
tccataccgt aaacgatgaa tgctaagtgt tggagggttt ccgcccttca gtgctgcagc    720
taacgcatta agcattccgc ctggggagta cggccgcaag gctgaaactc aaaggaattg    780
acggggcccc gcacaagcgg tggagcatgt ggtttaattc gaagctacgc gaagaacctt    840
accaggtctt gacatactat gcaaatctaa gagattagac gttcccttcg ggacatgga    900 tacaggtggt gcatggttgt cgtcagctcg tgtcgtgaga tgttgggtta agtcccgcaa    960
cgagcgcaac ccttattatc agttgccagc attaagttgg gcactctggt gagactgccg   1020
gtgacaaacc ggaggaaggt ggggatgacg tcaaatcatc atgccccta tgacctgggc    1080 tacacacgtg ctacaatgga tggtacaacg agttgcgaac tcgcgagagt aagctaatct   1140
cttaaagcca ttctcagttc ggattgtagg ctgcaactcg cctacatgaa gtcggaatcg   1200
ctagtaatcg cggatcagca tgccgcggtg aatacgttcc cgggccttgt acacaccgcc   1260
cgtcacacca tgagagtttg taacacccaa agtcggtggg gtaaccttt aggaaccagc    1320 cgcctaaggt gggacagatg attagggtga agtcgtacag aggtaacc                 1368
```